(12) United States Patent
Fast et al.

(10) Patent No.: US 7,939,282 B2
(45) Date of Patent: May 10, 2011

(54) METHODS FOR DETECTING SEPSIS

(75) Inventors: Loren D. Fast, Foster, RI (US); Yow-Pin Lim, East Providence, RI (US)

(73) Assignee: Rhode Island Hospital, Providence, RI (US)

( * ) Notice: Subject to any disclaimer, the term of this patent is extended or adjusted under 35 U.S.C. 154(b) by 230 days.

(21) Appl. No.: 11/255,634

(22) Filed: Oct. 20, 2005

(65) Prior Publication Data

US 2006/0110774 A1 May 25, 2006

Related U.S. Application Data

(60) Provisional application No. 60/621,922, filed on Oct. 21, 2004.

(51) Int. Cl.
| | |
|---|---|
| *G01N 33/53* | (2006.01) |
| *G01N 33/543* | (2006.01) |
| *G01N 33/563* | (2006.01) |
| *G01N 33/573* | (2006.01) |
| *G01N 33/577* | (2006.01) |
| *C07K 16/18* | (2006.01) |
| *C07K 16/40* | (2006.01) |

(52) U.S. Cl. ...... 435/7.4; 435/7.24; 435/7.92; 435/7.93; 435/7.94; 435/70.21; 436/501; 436/512; 436/518; 436/547; 436/548; 436/63; 530/387.9; 530/388.26; 530/388.73; 530/388.75; 530/389.1; 530/389.6

(58) Field of Classification Search ............... 435/7.24, 435/7.4, 7.8, 7.92, 7.93, 70.21, 7.94; 436/501, 436/518, 63, 547, 548, 512; 530/387.9, 388.26, 530/388.73, 388.75, 389.1, 389.6
See application file for complete search history.

(56) References Cited

FOREIGN PATENT DOCUMENTS

| WO | 97/40151 | * 10/1997 |
| WO | 99/54737 | * 10/1999 |

OTHER PUBLICATIONS

Sayers et al., 1996. Cloning and expression of a second human natural killer cell granule tryptase, HNK-Tryp-2/granzyme 3. Journal of Leukocyte Biology 59: 763-768.*
Campbell, 1984. Monoclonal Antibody Technology, Elsevier, Amsterdam. pp. 1-4 and 29.*
Hameed et al., 1988. Characterization of three serine esterases isolated from human IL-2 activated killer cells. Journal of Immunology 141: 3142-3147.*
Lauw et al., 2000. Soluble granzymes are released during human endotoxemia and in patients with severe infection due to gram-negative bacteria. Journal of Infectious Diseases 182: 206-213.*
Przetak et al., 1995. Cloning of cDNA for human granzyme 3. FEBS Letters 364: 268-271.*
Grossman et al., 2003. The orphan granzymes of humans and mice. Current Opinion in Immunology 15: 544-552.*
Bade et al. *Eur. J. Immunol.*, 35:2940-2948 (2005).
Hanna et al. *Protein Express. Purif.*, 4(5):398-404 (1993).
Levy et al. *Crit. Care Med.*, 31(4):1250-1256 (2003).
Lim et al. *J. Infect. Dis.*, 188:919-926 (2003).
Rivers et al. *N. Engl. J. Med.*, 345(19):1368-1377 (2001).

* cited by examiner

*Primary Examiner* — Shafiqul Haq
*Assistant Examiner* — James L Grun
(74) *Attorney, Agent, or Firm* — Mintz Levin Cohn Ferris Glovsky and Popeo, P.C.; Ingrid A. Beattie

(57) ABSTRACT

Compositions and methods for detecting sepsis by contacting a subject-derived sample with a ligand that binds to GRK and determining the concentration of GRK in the sample. An increase in the concentration of GRK compared to that of a normal, healthy control sample indicates that the subject from which the sample is obtained is suffering from or at risk of developing sepsis.

19 Claims, 9 Drawing Sheets

SEQUENCE LISTING

<160> NUMBER OF SEQ ID NOS: 5

<210> SEQ ID NO 1
<211> LENGTH: 264
<212> TYPE: PRT
<213> ORGANISM: Homo sapiens

<400> SEQUENCE: 1

```
Met Thr Lys Phe Ser Ser Phe Ser Leu Phe Phe Leu Ile Val Gly Ala
1               5                   10                  15

Tyr Met Thr His Val Cys Phe Asn Met Glu Ile Ile Gly Gly Lys Glu
            20                  25                  30

Val Ser Pro His Ser Arg Pro Phe Met Ala Ser Ile Gln Tyr Gly Gly
        35                  40                  45

His His Val Cys Gly Gly Val Leu Ile Asp Pro Gln Trp Val Leu Thr
    50                  55                  60

Ala Ala His Cys Gln Tyr Arg Phe Thr Lys Gly Gln Ser Pro Thr Val
65                  70                  75                  80

Val Leu Gly Ala His Ser Leu Ser Lys Asn Glu Ala Ser Lys Gln Thr
                85                  90                  95

Leu Glu Ile Lys Lys Phe Ile Pro Phe Ser Arg Val Thr Ser Asp Pro
            100                 105                 110

Gln Ser Asn Asp Ile Met Leu Val Lys Leu Gln Thr Ala Ala Lys Leu
        115                 120                 125

Asn Lys His Val Lys Met Leu His Ile Arg Ser Lys Thr Ser Leu Arg
    130                 135                 140

Ser Gly Thr Lys Cys Lys Val Thr Gly Trp Gly Ala Thr Asp Pro Asp
145                 150                 155                 160

Ser Leu Arg Pro Ser Asp Thr Leu Arg Glu Val Thr Val Thr Val Leu
                165                 170                 175

Ser Arg Lys Leu Cys Asn Ser Gln Ser Tyr Tyr Asn Gly Asp Pro Phe
            180                 185                 190

Ile Thr Lys Asp Met Val Cys Ala Gly Asp Ala Lys Gly Gln Lys Asp
        195                 200                 205

Ser Cys Lys Gly Asp Ser Gly Gly Pro Leu Ile Cys Lys Gly Val Phe
    210                 215                 220

His Ala Ile Val Ser Gly Gly His Glu Cys Gly Val Ala Thr Lys Pro
225                 230                 235                 240

Gly Ile Tyr Thr Leu Leu Thr Lys Lys Tyr Gln Thr Trp Ile Lys Ser
                245                 250                 255

Asn Leu Val Pro Pro His Thr Asn
            260
```

<210> SEQ ID NO 2
<211> LENGTH: 1040
<212> TYPE: DNA
<213> ORGANISM: Homo sapiens

<400> SEQUENCE: 2

```
aacacatttc atctgggctt cttaaatcta aatctttaaa atgactaagt tttcttcctt      60
ttctctgttt ttcctaatag ttggggctta tatgactcat gtgtgtttca atatggaaat    120
tattggaggg aaagaagtgt cacctcattc caggccattt atggcctcca tccagtatgg    180
```

```
cggacatcac gtttgtggag gtgttctgat tgatccacag tgggtgctga cagcagccca    240
ctgccaatat cggtttacca aaggccagtc tcccactgtg gttttaggcg cacactctct    300
ctcaaagaat gaggcctcca acaaacact ggagatcaaa aaatttatac cattctcaag     360
agttacatca gatcctcaat caaatgatat catgctggtt aagcttcaaa cagccgcaaa    420
actcaataaa catgtcaaga tgctccacat aagatccaaa acctctctta gatctggaac    480
caaatgcaag gttactggct ggggagccac cgatccagat tcattaagac cttctgacac    540
cctgcgagaa gtcactgtta ctgtcctaag tcgaaaactt tgcaacagcc aaagttacta    600
caacggcgac cctttatca ccaaagacat ggtctgtgca ggagatgcca aaggccagaa     660
ggattcctgt aagggtgact caggggggccc cttgatctgt aaaggtgtct tccacgctat   720
agtctctgga ggtcatgaat gtggtgttgc cacaaagcct ggaatctaca ccctgttaac    780
caagaaatac cagacttgga tcaaaagcaa ccttgtcccg cctcatacaa attaagttac    840
aaataatttt attggatgca cttgcttctt ttttcctaat atgctcgcag gttagagttg    900
ggtgtaagta aagcagagca catatggggt ccatttttgc acttgtaagt cattttatta    960
aggaatcaag ttcttttttca cttgtatcac tgatgtattt ctaccatgct ggttttattc   1020
taaataaaat ttagaagact                                                 1040

<210> SEQ ID NO 3
<211> LENGTH: 16
<212> TYPE: PRT
<213> ORGANISM: Artificial Sequence
<220> FEATURE:
<223> OTHER INFORMATION: chemically synthesized

<400> SEQUENCE: 3

Asn Ser Gln Ser Tyr Tyr Asn Gly Asp Pro Phe Ile Thr Lys Asp Cys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: chemically synthesized

<400> SEQUENCE: 4

Asn Asp Arg Asn His Tyr Asn Phe Asn Pro Val Ile Gly Met Asn Ser
1               5                   10                  15

<210> SEQ ID NO 5
<211> LENGTH: 16
<212> TYPE: PRT
<213> ORGANISM: Homo sapiens

<400> SEQUENCE: 5

Asn Ser Gln Ser Tyr Tyr Asn Gly Asp Pro Phe Ile Thr Lys Asp Met
1               5                   10                  15
```

METHODS FOR DETECTING SEPSIS

RELATED APPLICATIONS

This application claims priority to U.S. provisional patent application No. 60/621,922, filed on Oct. 21, 2004, the entire contents of which are hereby incorporated by reference.

FIELD OF THE INVENTION

This invention relates to methods of detecting sepsis.

BACKGROUND OF THE INVENTION

Sepsis is a systemic response to infection. It can cause organ failure and death in severe cases. Severe sepsis is one of the most significant challenges in health care. Mortality remains high. Early diagnosis and prompt treatment greatly improve survival. However, an early sepsis condition or an infection with a risk of leading to sepsis has proven difficult to detect.

SUMMARY OF THE INVENTION

The invention features methods and compositions for detecting sepsis, e.g., early stage sepsis in a mammal. The method includes the steps of providing a patient-derived clinical sample and contacting the sample with a detectable label that preferentially binds to serine protease granzyme K (GRK, GRMK, tryptase 2, or granzyme 3), e.g., human GRK, or a fragment thereof. The level of GRK is a predictor of early sepsis. The clinical sample is a sample of bodily fluid or bodily tissue from a normal (uninfected individual) or a sample from an individual suffering from or at risk of developing sepsis. Patients at risk of developing severe sepsis include critically ill patients such as those identified as having severe CAP (community-acquired pneumonia), intra-abdominal surgery, meningitis, chronic diseases (e.g., diabetes, heart failure, chronic renal failure, and COPD), a compromised immune status (HIV/AIDS, use of cytotoxic and immunosuppressive agents, malignant neoplasms, and alcoholism), cellulitis, or urinary tract infection. At even greater risk are those identified as being of advanced age (greater than 65 years of age), underlying comorbidity, greater than normal body weight, and disease characteristics such as shock, hypoxemia, organ system failures, disseminated intravascular coagulation.

An increase in the level of GRK in a patient-derived sample compared to that of a normal control (e.g., a sample or pool of samples of same or similar tissue or fluid obtained from normal, healthy individuals) indicates that the tested individual is suffering from sepsis, e.g., an early stage of sepsis, or is at risk of developing sepsis.

The patient-derived sample is preferably a volume of blood, plasma, serum, urine, saliva, or other bodily fluid or tissue from a mammal, e.g., a human subject, dog, wolf, coyote, cat, cow, sheep, horse, goat, mouse, rat, or other animal such as another member of an avian species or rodent species.

The method includes a step of detecting a GRK antigen by contacting the sample with a GRK-specific ligand such as an antibody or GRK binding fragment thereof. Such antibodies include polyclonal and monoclonal antibodies that bind to a GRK epitope of human GRK, e.g., NSQSYYNGDPFITKDM (residues 182-197 of SEQ ID NO:1) or residues 189-205 of SEQ ID NO:1). The ligand is an antibody or a fragment thereof. Preferably, the epitope to which the ligand binds comprises, consists essentially of, or consists of residues 182-205 of SEQ ID NO: 1, or any 8, 9, 10, 11, or 12 residue fragment thereof. Such antibodies are generated by immunizing an animal with the above-defined peptide and selecting for a polyclonal or monoclonal antibody according to standard methods.

In some embodiments, the antibody is a monoclonal antibody. Alternatively, the antibody is a polyclonal antibody. In other embodiments, the antibody is a mixture of monospecific antibodies. Preferably, the determining step is carried out by immunoassay. Preferably, the ligand detects free GRK and bound GRK, said bound GRK being a component of a GRK-inhibitor compound.

Also within the invention is an antibody specific for GRK. The antibody binds to an epitope present on both free and complexed GRK. For example, the antibody binds to an epitope comprising residues 182-197 of SEQ ID NO:1 or an epitope comprising residues 189-205 of SEQ ID NO: 1. In preferred embodiments, the antibody binds to both human and mouse GRK. The antibody is an IgM, IgM, or IgG isotype antibody, such as an IgG1, 2, or 3 isotype.

The method optionally includes the step of determining the concentration of inter-alpha inhibitor proteins (IaIp), wherein an inverse correlation between an increase in GRK and decrease in IaIp indicates a diagnosis of early sepsis.

A method of making a sepsis-detection reagent such as those described above is carried out by immunizing an animal with a peptide comprising a GRK-specific sequence such as a peptide of 8, 9, 10, 11, 12, 20, 30, 40, 50 or more (up to the full length of mature GRK). For example, the immunizing peptide has a sequence selected from consecutive residues of 182-205 of SEQ ID NO:1.

Also within the invention is a kit for diagnosis of sepsis. The kit contains a ligand that binds to an epitope of the GRK, a detectable label, and instructions regarding detecting a difference in the level or amount of GRK in a patient sample for the purpose of detecting sepsis.

Other features and advantages of the invention will be apparent from the following description of the preferred embodiments thereof, and from the claims.

BRIEF DESCRIPTION OF THE DRAWINGS

FIG. 8A shows data from Group ED (n=14; Spearman; r=−0.5551; P=0.0394) and FIG. 8B shows data from Group CT (n=25; Spearman; r=0.197; P=0.3451).

DETAILED DESCRIPTION OF THE INVENTION

Figure 1:
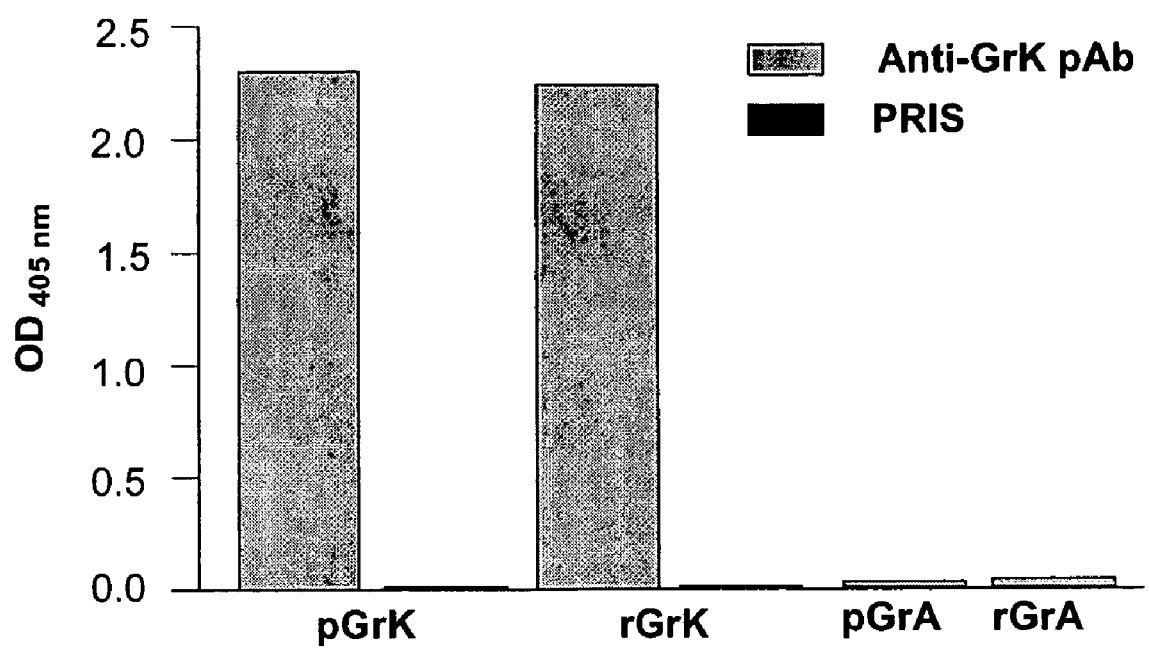
FIG. 1 is a bar graph showing the specificity of an anti-GRK polyclonal antibody in ELISA. Microplates were coated with synthetic peptides derived from human GRK and GrA (pGRK, pGrA) or human recombinant granzymes (rGRK, rGrA) and incubated with rabbit anti-GRK polyclonal antibody (pAb) or pre-immune serum (PRIS) as a negative control.

Sepsis is a consequence of a dysregulated inflammatory immune response that occurs as a result of systemic microbial infections. The mortality associated with sepsis remains high despite antimicrobial therapy and intensive care. The heterogeneous nature of sepsis often makes it difficult to diagnose. Misdiagnoses and inappropriate treatments because of the variety of infectious agents, different sources of infection and individual differences contribute to the increased mortality associated with sepsis. Accurate diagnosis sepsis at early time points using the methods described herein permits the early implementation of early goal directed therapy and reduces mortality. This approach is implemented by the identification of an biomarker (GRK) to stage early sepsis. Intervention at this early stage reduces mortality.

Inter-alpha inhibitor proteins (IaIp) are serpin family members found at relatively high concentration in human plasma. IaIp are composed of heavy and light polypeptide subunits that are covalently linked by a chondroitin sulphate chain. The light chain (also termed 'bikunin'=bi-kunitz inhibitor=inhibitor with two Kunitz domains) is responsible for the serine protease inhibitory activity of the molecules. The major forms found in human plasma are Inter-alpha Inhibitor (IaI), which consist of two heavy chains (H1 & H2) and a single light chain, and Pre-alpha Inhibitor (PaI), which consist of one heavy (H3) and one light chain. The relatively high levels of IaIp normally circulating in plasma and the fact that no person with complete absence of IaIp has ever been detected, suggests that these proteins have an essential physiological role which remains to be established. The data described herein revealed a significant decrease of plasma IaIp levels in adult patients and newborns with clinically proven sepsis, and established a correlation between the levels of IaIp and mortality in adult septic patients.

To quantitatively analyze the levels of GRK in biological samples, a specific antibody (pAb) against human GRK was made. Using this antibody, a competitive immunoassay for the measurement of GRK levels in plasma was developed. The assay was used to determine and compare the levels of GRK in healthy controls (HC) and two groups of septic patients: patients with early symptoms of sepsis admitted in the Emergency Department (Group ED) and patients enrolled in clinical trials (Group CT) of severe sepsis. The molecular forms of GRK in these plasma samples were defined by immunoblot analysis using GRK specific Ab.

GRK levels were significantly increased in Group ED and significantly decreased in Group CT compared to HC. IaIp levels were decreased in both septic groups. Thus, the biomarker of a decreased level of GRK is useful to identify those individuals with early sepsis, i.e., those that benefit most from immediate intervention.

Immunoblot analysis confirmed the presence of GRK in high molecular weight complexes in healthy controls whereas various reactive lower molecular weight complexes and free GRK were identified in plasma of both sepsis groups. The specific GRK binding reagents described herein detect both free GRK as well as GRK complexes, thereby providing data on total GRK levels in a patient as opposed to a subset of GRK (i.e., only free GRK). These results indicated that the level of total GRK is useful as an early marker and improved marker in patients developing sepsis. Information regarding the amount of total GRK in a patient compared to a normal control or over time facilitates early intervention that is crucial in reducing sepsis related mortality.

Analysis of Granzyme K in Patients with Early Symptoms of Sepsis

An ELISA assay was developed to measure the levels of GRK, a protease, in human plasma. Results obtained using the assay demonstrated significant changes in the level of GRK at different stages during sepsis. In combination with the measurement of inter-alpha trypsin inhibitor (ITI) levels, the results of these assays identified early stages of sepsis. Detection of sepsis at an early stage of development permits early intervention/therapy when the disease is still controllable.

Decreased levels of protein inhibitors, Inter-α-inhibitor proteins (IaIp) were associated with the sepsis patients that as a group exhibited the highest level of mortality. Although these results found a correlation with decreased IaIp levels and increased mortality from sepsis, it did not provide an explanation for the relationship. Thus, studies were carried out to determine whether decreased levels of IaIp resulted in or correlated with increased levels of GRK. Because no assay was available to measure GRK, an immunoassay such as an ELISA to measure GRK levels was developed. The use of herein-described assay demonstrated that emergency room patients with symptoms of early sepsis exhibited low levels of IaIp but significantly increased levels of GRK while sepsis patients enrolled in a clinical trial (indicative of those with advanced or severe sepsis), which would usually occur a day or two after admittance to the emergency room exhibited, significantly lower levels of both IaIp and GRK. Because of the significant mortality associated with sepsis and the finding that early treatment of sepsis is advantageous to survival, the assay was used to define the stage of sepsis facilitating the establishment of the protocols for treating sepsis at any given stage of sepsis. Prior to the invention, no assays were available to identify early sepsis or to define early stages of sepsis to distinguish early sepsis from advanced or severe sepsis. Severe sepsis is a condition known in the art and is e.g., characterized by at least one documented organ dysfunction (Levy et al., 2003, Crit. Care Med. 31: 1250-1256; herein incorporated by reference).

The GRK ligands in the assay preferentially and/or specifically bind to human GRK, the amino acid sequence of which is shown below.

Granzyme Proteins

Granzymes (Grs) belong to the family of granule associated serine proteases that are expressed by cytotoxic T lymphocytes (CTL) and Natural killer (NK) cells and play important role in target cell apoptosis. Grs cleave a number of extracellular matrix proteins, thereby facilitating migration of CTL and NK cells through extracellular tissues, and induce cytokine secretion and directly activating various cytokines. GRK plays a role in inflammation responses and has pro-inflammatory properties A significant decrease of plasma level of natural serine proteases inhibitors (inter-alpha inhibitor proteins, IaIp) is found in septic patients. IaIp is shown to be a physiological inhibitor of GRK. Studies were carried out to determine whether GRK, as a protease, plays a role in pathogenesis of sepsis.

GRK-Specific Antibodies

Human GRK was used to generate GRK-specific antibodies. For example, a peptide with the amino acid sequence, 182-197 NSQSYYNGDPFITKDM of SEQ ID NO:1 (SEQ

TABLE 1

Protein Sequence 264AA NP 002095.1 (underline = mature protein)

MTKFSSFSLF FLIVGAYMTH VCFNMEIIGG KEVSPHSRPF MASIQYGGHH VCGGVLIDPQ WVLTAAHCQY

RFTKGQSPTV VLGAHSLSKN EASKQTLEIK KFIPFSRVTS DPQSNDIMLV KLQTAAKLNK HVKMLHIRSK

TSLRSGTKCK VTGWGATDPD SLRPSDTLRE VTVTVLSRKL CNSQSYYNGD PFITKDMVCA GDAKGQKDSC

KGDSGGPLIC KGVFHAIVSG GHECGVATKP GIYTLLTKKY QTWIKSNLVP PHTN (SEQ ID NO: 1)

TABLE 2

DNA Sequence Open Reading Frame underlined: 41 to 835 NM 002104.1

AACACATTTC ATCTGGGCTT CTTAAATCTA AATCTTTAAA ATGACTAAGT TTTCTTCCTT TTCTCTGTTT

TTCCTAATAG TTGGGGCTTA TATGACTCAT GTGTGTTTCA ATATGGAAAT TATTGGAGGG AAAGAAGTGT

CACCTCATTC CAGGCCATTT ATGGCCTCCA TCCAGTATGG CGGACATCAC GTTTGTGGAG GTGTTCTGAT

TGATCCACAG TGGGTGCTGA CAGCAGCCCA CTGCCAATAT CGGTTTACCA AAGGCCAGTC TCCCACTGTG

GTTTTAGGCG CACACTCTCT CTCAAAGAAT GAGGCCTCCA AACAAACACT GGAGATCAAA AAATTTATAC

CATTCTCAAG AGTTACATCA GATCCTCAAT CAAATGATAT CATGCTGGTT AAGCTTCAAA CAGCCGCAAA

ACTCAATAAA CATGTCAAGA TGCTCCACAT AAGATCCAAA ACCTCTCTTA GATCTGGAAC CAAATGCAAG

GTTACTGGCT GGGGAGCCAC CGATCCAGAT TCATTAAGAC CTTCTGACAC CCTGCGAGAA GTCACTGTTA

CTGTCCTAAG TCGAAAACTT TGCAACAGCC AAAGTTACTA CAACGGCGAC CCTTTTATCA CCAAAGACAT

GGTCTGTGCA GGAGATGCCA AAGGCCAGAA GGATTCCTGT AAGGGTGACT CAGGGGGCCC CTTGATCTGT

AAAGGTGTCT TCCACGCTAT AGTCTCTGGA GGTCATGAAT GTGGTGTTGC CACAAAGCCT GGAATCTACA

CCCTGTTAAC CAAGAAATAC CAGACTTGGA TCAAAAGCAA CCTTGTCCCG CCTCATACAA ATTAAGTTAC

AAATAATTTT ATTGGATGCA CTTGCTTCTT TTTTCCTAAT ATGCTCGCAG GTTAGAGTTG GGTGTAAGTA

AAGCAGAGCA CATATGGGGT CCATTTTTGC ACTTGTAAGT CATTTTATTA AGGAATCAAG TTCTTTTTCA

CTTGTATCAC TGATGTATTT CTACCATGCT GGTTTTATTC TAAATAAAAT TTAGAAGACT (SEQ ID NO: 2)

ID NO: 5), a sequence unique to GRK was used to immunize rabbits. Polyclonal antisera as well as 20 monoclonal antibodies were generated using known methods. The antibodies were characterized, and an immunoassay to detect GRK levels in bodily fluids such as plasma was developed. Other GRK antibodies are commercially available and known in the art.

Reagents and Procedures

Synthetic peptides, NSQSYYNGDPFITKDC (pGRK: SEQ ID NO:3) and NDRNHYNFNPVIGMNS (pGrA; SEQ ID NO:4), derived from human Granzyme K and Granzyme A were synthesized using known methods or obtained from Sigma-Genosys (The Woodlands, Tex.). Recombinant human GRK (rGRK) and GrA (rGrA) were purchased from Alexis Biochemicals (San Diego, Calif.). All other chemicals were purchased from Sigma (St. Louis, Mo.) unless otherwise specified.

Cell Culture

The human IL-2 dependent NK cell line 92MI was obtained from the American Type Culture Collection (ATCC, Manassas, Va.). The cells were maintained in alpha minimum essential medium (Gibco, Grand Island, N.Y.), supplemented with 2 mM L-glutamine, 0.2 mM inositol, 0.1 mM 2-mercaptoethanol, 0.02 mM folic acid, 5% heat inactivated fetal calf serum (FCS) and horse serum. The cells were incubated in humidified air with 10% $CO_2$ at 37° C. and sub-cultured twice per week.

Purification of GRK from Human NK Cell Line (NK-GRK)

GRK was purified from cytotoxic granules of IL-2 dependent human NK cell line according to known methods, e.g., Hanna et al., 1993, Protein Express Purif 4:398-404.

Generation, Characterization and Purification of GRK Specific Polyclonal Antibody (pAb)

Polyclonal antibody against human GRK was generated in rabbits by immunizing with the synthetic peptide pGRK, corresponding to amino acid residues 189-205 of human GRK (SEQ ID NO:1) manufactured by Sigma-Genosys, The Woodlands, Tex. This sequence was identified using the MacVector software (Accelrys Inc, San Diego, Calif.) as a sequence unique to human GRK when compared to the sequence of human Granzyme A, Granzyme B or neutrophil elastase, cathepsin G or proteinase 3. It was also chosen from the sequence with the highest immunogenicity predicted by this software. Pre-immune serum (PRIS) was obtained prior to immunization. Three immunizations were performed at day 0, 14 and 28. Sera were collected and further characterized for its specificity.

Western Blot Analysis of Human GRK

Samples containing GRK: rGRK, NK-GRK or plasma samples were mixed with non-reducing SDS sample buffer, heated to 95° C. for 15 min, and separated by 12.5% SDS-PAGE. The immunodetection was performed using anti-GRK pAb followed by incubation with horseradish peroxidase (HRP)-conjugated goat anti-rabbit IgG (Biosource, Camarillo, Calif.). The blots were visualized by using Enhanced Chemiluminescence system (Pierce, Rockford, Ill). For the analysis of high molecular weight complex forms of GRK in plasma, samples were separated using 4-12% NuPAGE Bis-Tris gels according to the manufacturer's instruction (Invitrogen Corporation, Carlsbad, Calif.).

Direct Binding and Competitive Peptide Inhibition Assay

The specificity of the anti-GRK pAb was determined by a direct solid phase binding assay. pGRK and pGrA or rGRK and rGrA were immobilized onto 96-well microplates (Immulon 4, Dynex) in coating buffer (50 mM sodium bicarbonate, pH 9.6). Following blocking with 5% non-fat dried milk, anti-GRK pAb or PRIS diluted in PBS were added to the wells. The bound antibodies were detected by using HRP-conjugated goat anti-rabbit IgG and visualized by 1-Step ABTS substrate (Zymed, San Francisco, Calif.). The color change was measured at 405 nm on BioTek microplate reader (Bio-Tek Instruments, Winooski, Vt.). For the competitive inhibition assay, anti-GRK pAb was pre-incubated with various concentrations (from 0.01 to 10 ng/μL) of pGRK or pGrA at 37° C. for 45 min prior to being added to the microplates coated with rGRK.

Affinity Purification

Anti-GRK pAb was affinity purified from the rabbit antiserum by using immobilized pGRK to NHS-activated Sepharose column according to the manufacture's instruction (Amersham Bioscience, Piscataway, N.J.).

Granzyme K ELISA Immunoassay

A competitive ELISA using affinity purified anti-GRK pAb was performed as follows: pGRK (250 ng/well) was immobilized in coating buffer onto 96-well microplates overnight at 4° C. After coating, residual binding sites were blocked by 3% BSA. A serial dilution of pooled human plasma (healthy donors) in PBS was used to generate a standard curve on each plate. The concentration of GRK in this pooled human plasma was defined as 2000 Arbitrary Units (U)/mL. For the GRK levels analysis, 50 μL of diluted plasma samples (1:10 in PBS) or serially diluted standard plasma, were added to individual wells in triplicate along with 50 μl of anti-GRK pAb (0.25 mg/mL) and incubated for 1 h at 37° C. Subsequently, HRP-conjugated goat anti-rabbit IgG were added to the wells. 1-step ABTS was used as a substrate and absorbance was measured at 405 nm. The specificity of the developed ELISA was further evaluated by using pGrA or rGRK immobilized on the microplates.

Inter Alpha Inhibitor Proteins (IaIp) ELISA Immunoassay

Plasma levels of IaIp were quantitatively measured by sandwich ELISA using known methods such as that described by Lim et al., 2003, J. Infect. Dis., 2003; 188:919-926.

Clinical Samples

Blood samples of 41 healthy individuals were examined to establish the normal range of GRK levels in plasma. Blood samples from two septic patient groups were analyzed. The first group consisted of 15 patients delivered to the Emergency Department at Rhode Island Hospital (Group ED) with hypotension secondary to pneumonia or urosepsis. Each of these patients was identified and treated using the early-goal directed treatment guidelines for sepsis (Rivers et al., 2001, N. Engl. J. Med., 345:1368-1377; hereby incorporated by reference). These patients met the following criteria: a systolic blood pressure <90 mmHg after 2 liters of crystalloid infusion or a serum lactate >4 mmol/L. Monitoring of central venous pressure was performed in the ED which was used in titrating correct amounts of subsequent crystalloid and dobutamine in achieving normotension. These patients were subsequently transferred to the medical intensive care unit (ICU) for further treatment. Collected plasma from patients at the time of admission in the ED was used for the GRK assay. This represents the samples from the patients with the early stage of sepsis when the diagnosis was established at the time of admission.

The second septic group consisted of 25 severe septic patients enrolled in the phase III multicenter septic clinical trial of an experimental therapeutic agent (Group CT). Blood samples were obtained at study entry within 24 hours of the onset of severe sepsis (according to the consensus definitions established at the American College of Chest Physicians/Society of Critical Care Medicine Consensus conference (Levy et al., 2003, Crit. Care Med. 31 1250-1256; herein incorporated by reference). Plasma was separated from the blood by centrifugation, transported to the research laboratory, and stored at −80° C.

Statistical Analysis

Student's t test was used to analyze the significance of the plasma GRK levels between the septic groups and healthy controls. All data were presented as mean values±SD. Correlation was performed using the Spearman test. A P value <0.05 was considered as statistically significant.

Characterization of Anti-GRK pAb

Figure 2:
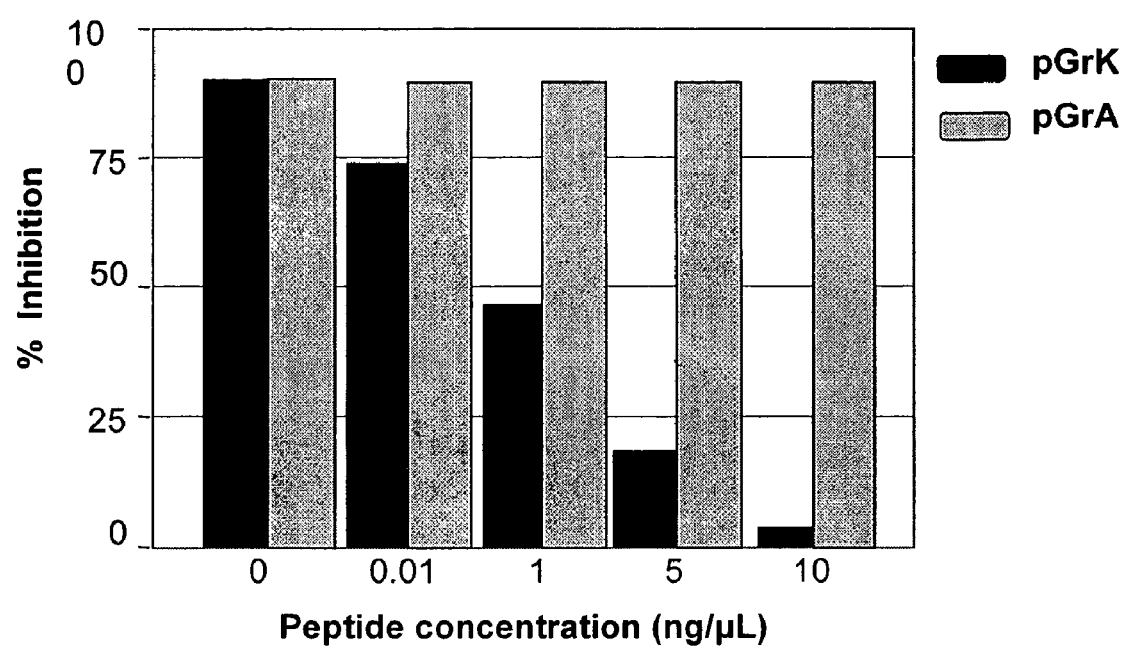
FIG. 2 is a bar graph showing the competitive effects of synthetic peptide pGRK. Various concentrations (from 0.01 to 10 ng/µL) of synthetic peptides, pGRK and pGrA were added to anti-GRK pAb and measured for their effect on the binding of the antibody to rGRK. The synthetic peptide pGRK competitively inhibited the binding of anti-GRK pAb to immobilized rGRK in concentration dependent manner. A complete inhibition of antibody binding was achieved at 10 ng/µL of pGRK while control pGrA had no significant effect.

The specificity of anti-GRK pAb was determined in a direct binding ELISA using immobilized peptides, pGRK and pGrA, and with recombinant granzymes, rGRK and rGrA as shown in FIG. 1. Anti-GRK pAb bound specifically to pGRK and rGRK but not to pGrA or rGrA. No binding was observed in the control pre-immune serum. To verify the specificity of this antibody, a competitive binding assay was performed. pGRK was able to inhibit the binding of anti-GRK pAb to rGRK immobilized on the 96-well microplates in a concentration dependent manner. A complete inhibition of antibody binding was achieved at 10 ng/μL of pGRK. No significant inhibition was observed with control pGrA (FIG. 2). These results demonstrated that anti-GRK pAb was specifically directed against unique peptide sequence corresponding to human GRK. The anti-GRK pAb was further affinity purified and used in Western blot and GRK ELISA.

Detection of Native Form of GRK from Human NK Cell Line

Figure 3A:
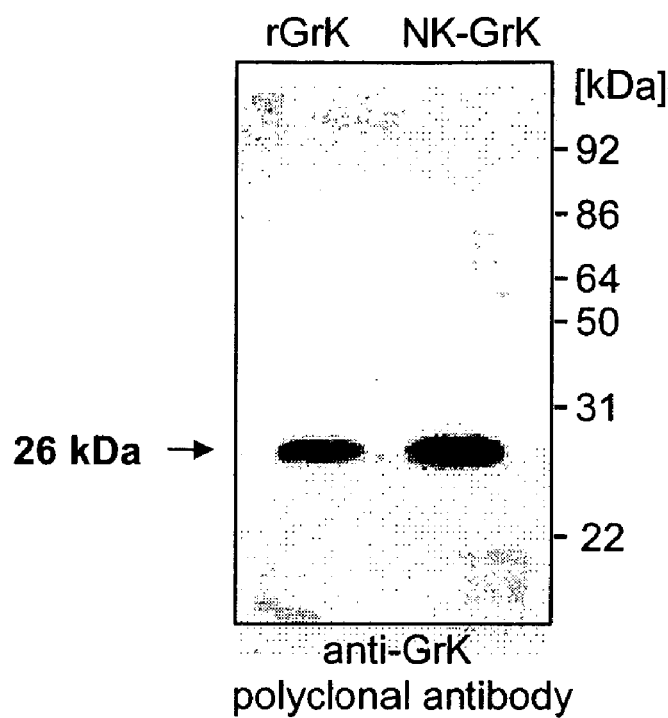
FIGS. 3A and 3B are photographs of electrophoretic gels showing the results of a Western Blot assay. The specificity of anti-GRK polyclonal antibody defined by Western blot analysis with human recombinant GRK (rGRK) and native GRK purified from human NK cells cytotoxic granules (NK-GRK). An identical 26 kDa reactive band was specifically recognized by anti-GRK GRK pAb in both, rGRK and NK-GRK (FIG. 3A). Pre-immune rabbit serum (PRIS) was used as a negative control (FIG. 3B).
Figure 3B:
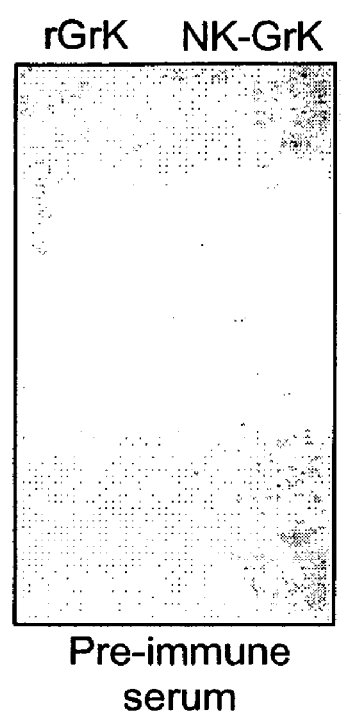

Granzymes (Grz) are expressed by CTL and NK cells and stored in their cytotoxic granules until degranulation. To identify the native form of GRK and to demonstrate the ability of anti-GRK pAb to bind GRK in its native form, GRK was purified from cytotoxic granules obtained from human IL-2 dependent NK cell line. Human rGRK was included as a positive control. The results of Western blot analysis using affinity purified anti-GRK pAb showed an identical 26 kDa reactive band in both, GRK purified from the human NK cell line and human rGRK (FIG. 3A). PRIS was used as a negative control (FIG. 3B). The results further confirmed the specificity of anti-GRK pAb and demonstrated its ability to bind native human GRK.

Development of a Competitive ELISA Using Anti-GRK pAb

Figure 4:
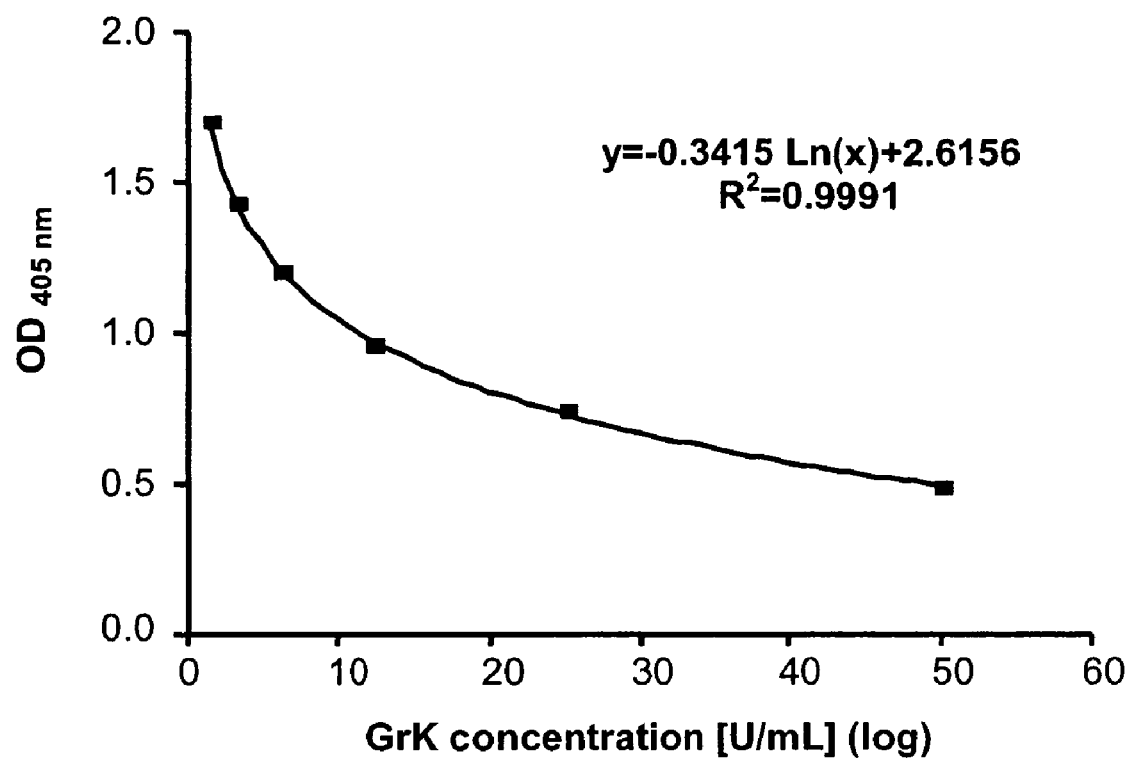
FIG. 4 is a line graph showing a standard curve of GRK assay. The curve was established by using serially diluted pooled human plasma with defined amount of GRK. The concentration of GRK was defined as 2000 Arbitrary Units/mL (U/mL) in the pooled human plasma. The detection range of the GRK assay was 1.5-100 U/mL. The Coefficient of Variation (CV) between three separate experiments was less than 10%.

To measure the levels of GRK in biological fluids such as plasma, a novel competitive ELISA using affinity purified anti-GRK pAb was developed. The immunoassay was based on the ability of GRK in plasma samples to block the binding of anti-GRK pAb to immobilized pGRK. Substitution of pGRK by rGRK showed similar results. A standard curve was established by a serial dilution of pooled human plasma (FIG. 4). The detection range of the GRK assay was 1.5-100 U/mL. The Coefficient of Variation (CV) between three separate experiments was less than 10%.

GRK Levels in Plasma of Septic Patients and Healthy Controls

Figure 5:
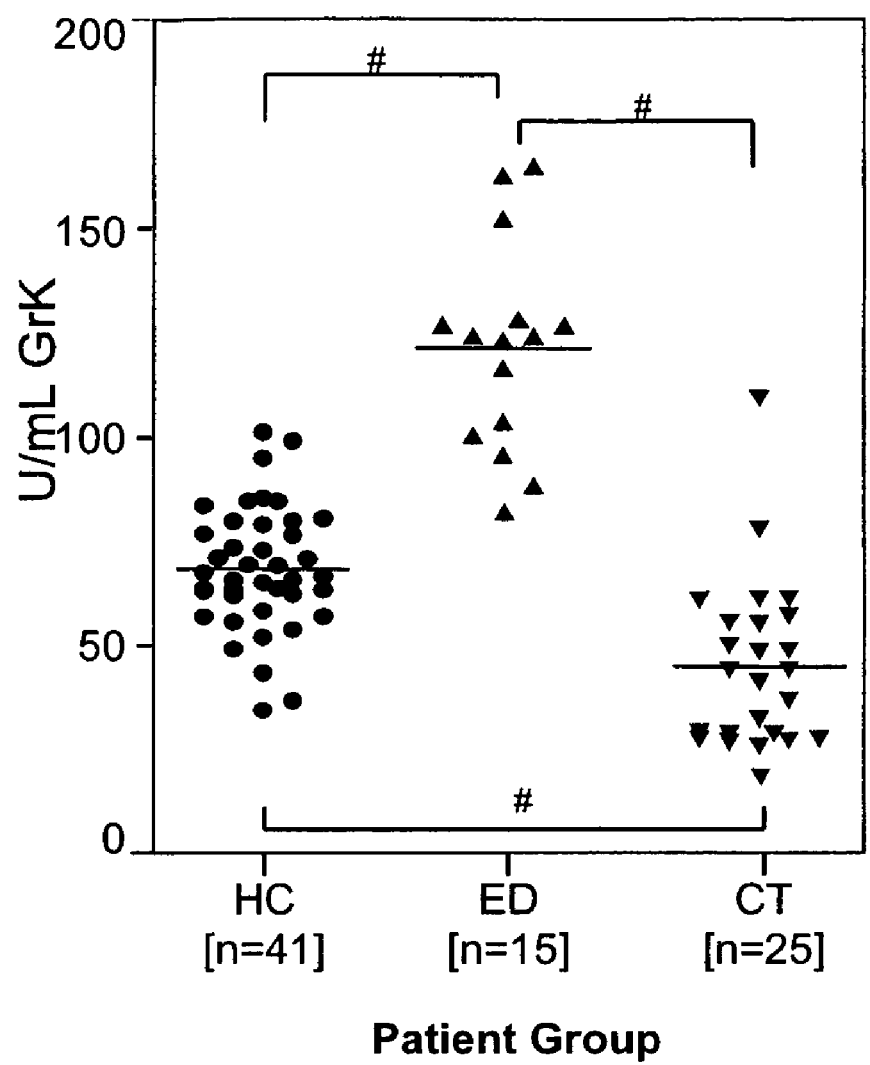
FIG. 5 is a scatter plot showing the plasma levels of GRK in healthy controls (HC), septic patients from the Emergency Department (Group ED) and septic clinical trials (Group CT). GRK levels were determined by the GRK specific ELISA described herein. Samples were assayed in triplicate, and the levels are expressed in Arbitrary Units/mL (U/mL). The differences between the means of septic groups (ED or CT) and HC were statistically significant (#P<0.0001). Statistically significant difference was also found between both septic groups (ED vs CT, #P<0.0001).

The developed competitive assay was used to measure the levels of GRK in plasma samples from healthy controls (HC) and septic patients exhibiting early symptoms of sepsis when admitted to the Emergency Department (Group ED) and septic patients with severe sepsis enrolled in a clinical trial (Group CT). The results indicated that the levels of GRK were significantly increased in Group ED (mean±SD=123.4±6.61 U/mL, n=15) and significantly decreased in Group CT (44.9±4.14 U/mL, n=25) compared to HC (69.14±2.39 U/mL, n=41) (FIG. 5). The differences between the plasma GRK levels in HC vs. Group ED and in HC vs. Group CT were statistically significant (P<0.0001). Statistically significant difference was also found between both septic groups (ED vs CT, P<0.0001).

Molecular Form of GRK in Human Plasma

In human plasma, serine proteases often appear in covalent complexes together with their respective inhibitors. In an effort to determine the molecular form of GRK present in plasma from healthy individuals and septic patients, samples were separated by 4-12% or 12.5% SDS-PAGE followed by Western blot analysis using anti-GRK pAb. The 4-12% SDS PAGE and subsequent Western blot analysis revealed that GRK circulates in healthy individuals in a complex form, resistant to SDS and heat, with a major bands of >250 and >150 kDa (FIG. 6A). In the plasma of septic patients analyzed, >250 kDa band was clearly absent. Enhanced levels of the 150 kDa band and additional bands corresponding to ~125, 98 and 60 kDa in the plasma of Group ED were observed while noticeably less of these GRK reactive bands were detected in the plasma of Group CT. Moreover, 12.5% SDS-PAGE and subsequent Western blot analysis showed a lower band of 26 kDa only in plasma of septic patients (Group ED and CT), but not in HC (FIG. 6B). The apparent 26 kDa band was similar in size with the GRK purified from human NK cells cytotoxic granules, suggesting the presence of systemic free GRK in septic patients.

IaIp Levels in Plasma of Septic Patients and Healthy Controls

Figure 7:
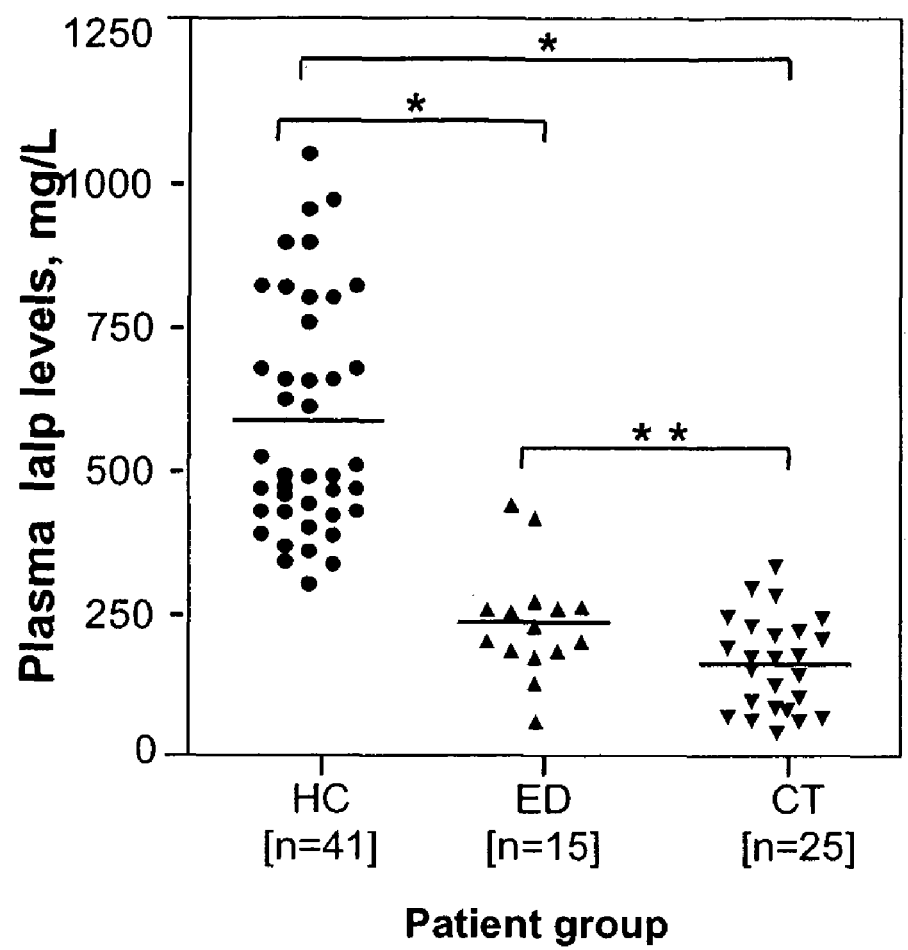
FIG. 7 is a scatter plot showing the plasma levels of Inter-alpha inhibitor proteins (IaIp) in HC, ED, and CT patient groups. IaIp levels were determined by a sandwich ELISA using mAb 69.26 and pAb against human IaIp. The lines represent the mean level for each group. A significant decrease of IaIp levels were found in both septic patient groups (Group ED and Group CT) compared to HC (*P<0.0001). The difference between two septic groups were also statistically significant (**P=0.0125).

Plasma IaIp levels of patients with sepsis are significantly decreased compared to normal controls. To determine whether the IaIp levels fluctuated with the stage of sepsis, IaIp levels were measured in the same set of samples assayed for GRK levels. The results demonstrated that plasma IaIp levels were significantly decreased in both septic patient groups: Group ED (249.6±24.31 mg/L, n=15) and Group CT (176.0±16.15 mg/L, n=25) compared to HC (597.1±31.69 mg/L, n=41). Statistically significant differences were found between the HC and either septic groups (P<0.0001). Differences between two septic groups (ED vs CT) were also statistically significant (p=0.0125) (FIG. 7).

Correlation between GRK and IaIp in Plasma of Septic Patient

Figure 8:
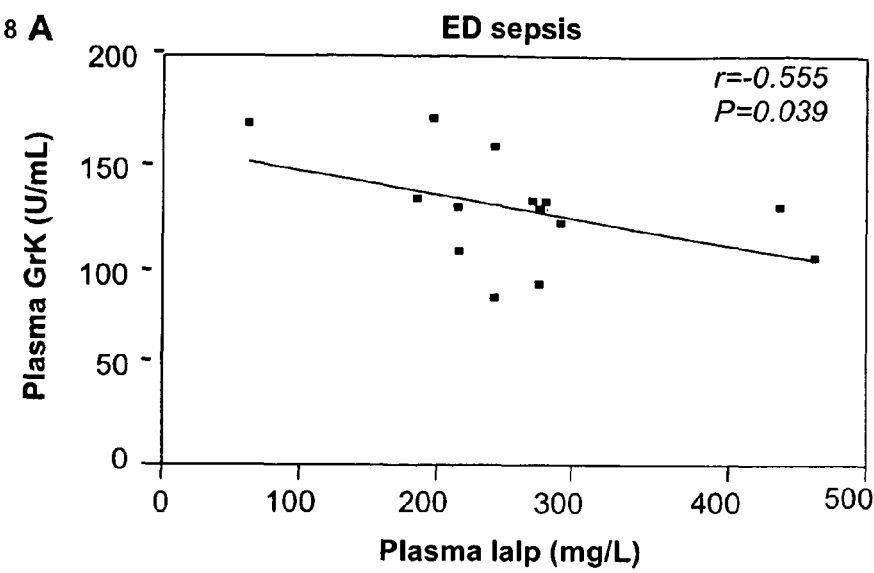
FIGS. 8A and 8B are scatter plots showing the correlation between plasma GRK and IaIp levels.
Figure 8:
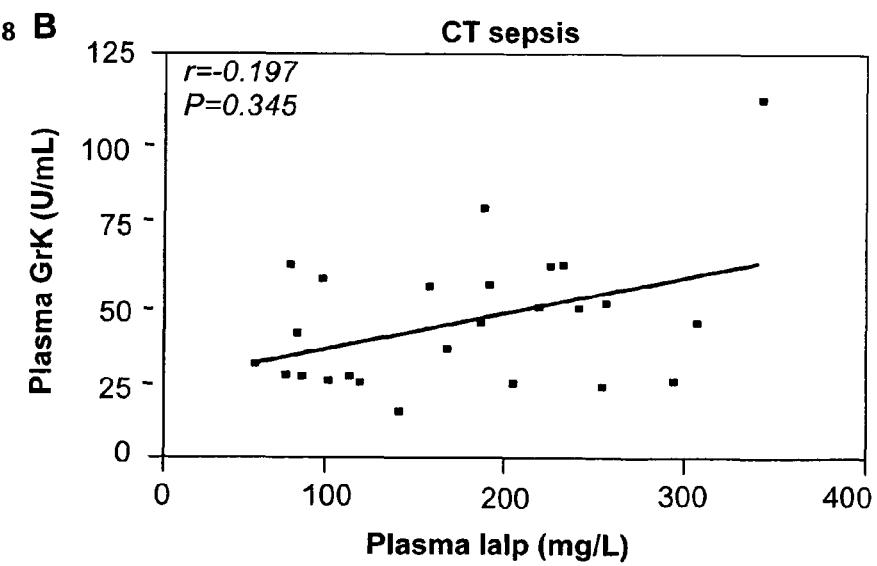

Measured plasma levels of GRK and IaIp from Group ED and Group CT were evaluated by the Spearman correlation test to determine the correlation between these proteins during sepsis progression. The results showed, an inverse correlation between the increase of GRK and decrease of IaIp levels in plasma of Group ED (n=14; Spearman; r=−0.5551; P=0.0394) (FIG. 8A). By contrast, no significant correlation between the GRK and IaIp levels of Group CT (n=25; Spearman; r=0.197; P=0.3451) was found (FIG. 8B).

Plasma Granzyme K Levels are Altered in Patients with Early Symptoms of Sepsis and Severe Sepsis Sepsis is not a single disease but a complex and heterogeneous process that can progress rapidly, leading to global tissue hypoxia, organ failure, and death. An early detection and early intervention was found to be crucial in reducing mortality from sepsis. The utility of a marker for sepsis that can identify patients at the early disease state when intervention can alter disease progression is therefore desirable.

Low constitutive plasma levels of Grz, serine proteases found in the cytotoxic granules of NK cells and CTL, have been observed. Because of their potent activity, excess protease inhibitors are usually present to inhibit these enzymes thereby preventing bystander effects. The absence of these inhibitors has been associated with disease pathology when increased serine protease activity is present. Decreased plasma levels of protease inhibitors in the presence of increased levels of serine proteases results in enhanced inflammatory responses resulting from the cleavage of specific substrates.

A highly specific GRK antibody was made and a competitive ELISA assay was developed to quantify the levels of GRK in biological samples. A constitutive level of GRK was observed in healthy controls and found to be present in high molecular weight (>250 and >150 kDa) complexes that were highly specific and stable to SDS and heat treatment. These results are consistent with the finding that IaIp are the physiological inhibitors of GRK as two IaIp include 250 kDa IaI and 125 kDa PaI.

Analysis of patients exhibiting symptoms of early sepsis found increased levels of GRK and decreased levels of IaIp. Biochemical analysis of the GRK present in these samples indicated the loss of the >250 kDa complex with a concordant increase of a number of different complexes of lower molecular weight. In addition, a free 26-kDa GRK form not found in healthy controls appeared in these patients. The result confirms the finding of decreased plasma levels of IaIp in septic patients in which a concomitant increase of IaIp-related fragments in urine was also observed. These findings are consistent with the proteolytic cleavage of IaIp, potentially a consequence of the release of proteases by activated neutrophils, or decreased production of IaIp. NK cells are the likely source of increased amounts of GRK as increased levels of GRK message is observed in activated NK cells. Inflammatory stimuli such as LPS have been shown to induce activation and proliferation of NK cells in vitro and in vivo injection of LPS into human volunteers induced a 5 fold increase in soluble GrA that peaked at 2 hours and an increase of soluble GrB that peaked at 6 hours.

Analysis of patients enrolled in a clinical trial for severe sepsis found significantly decreased GRK levels along with decreased levels of IaIp. Biochemical analysis of GRK indicated further degradation of the GRK complexes and a significant level of the free 26-kDa GRK form. These clinical trial patients were enrolled within 24 hours after the onset of severe sepsis in the ICU. Thus it is estimated that the blood collection from these patients occurred 24-72 hours after their admission to the emergency department. The rapid decrease in GRK levels associated with the progression of sepsis might be due to the combined effects of increased clearance and decreased GRK secretion at the time when sepsis has progressed. These findings are also consistent with the finding of a rapid decrease in Grz levels following a rapid increase in response to inflammatory stimuli. Taken together, the results indicate that measurement of GRK levels is a means for staging of sepsis and that increased levels of GRK are indicative of early sepsis.

The appearance of the free 26-kDa GRK form in the septic patients raises the possibility that the free GRK could impact the septic response. Increased levels of GrA and GrB have been observed in bacteremic melioidosis, and the GrA locus is closely linked to the GRK locus and both of these serine proteases act as tryptases. Incubation of human peripheral blood mononuclear cells with purified GrA has been found to induce the production of the proinflammatory cytokines, IL-6 and IL-8. One mechanism underlying the observed levels is that an innate response to infectious agent results in increased production of GRK, enhanced production of proteases cleaves IaIp, and decreased production of IaIp results in decreased levels of IaIp. The result of these events is the appearance of free uninhibited GRK which then induces increased levels of proinflammatory cytokines causing an amplification of the septic response.

The data described herein indicate that an anti-GRK Ab or mixture of antibodies raised against residues 182-197 and/or 189-205 of SEQ ID NO:1 is unique in its ability to recognize a specific epitope of GRK in both, free form and when complexed to inhibitors or other molecules and that the assay accurately measures the total levels of GRK (both free and complexed) in biological samples. The use of this antibody revealed that GRK appears in plasma of healthy individuals in a complex form. By contrast, free GRK was only found in patients with sepsis. Significantly increased levels of plasma GRK was found in patients with early symptoms of sepsis indicating that measuring plasma GRK levels is an effective tool to detect early sepsis.

The antibodies of the invention, e.g., rabbit polyclonal antibody with an epitope binding specificity of 182-197 NSQSYYNGDPFITKDM, is unique because it is able to detect GRK that is bound to inhibitor as well as free GRK. Other antibodies in the art (e.g., Bade et al, 2005, Eur. J. Immunol. 35:2940-2948) detect only free GRK. Thus, the ligands of the invention have an important clinical advantage in that they detect the total GRK level in an individual at risk of serious life-threatening illness or death.

Figure 6:
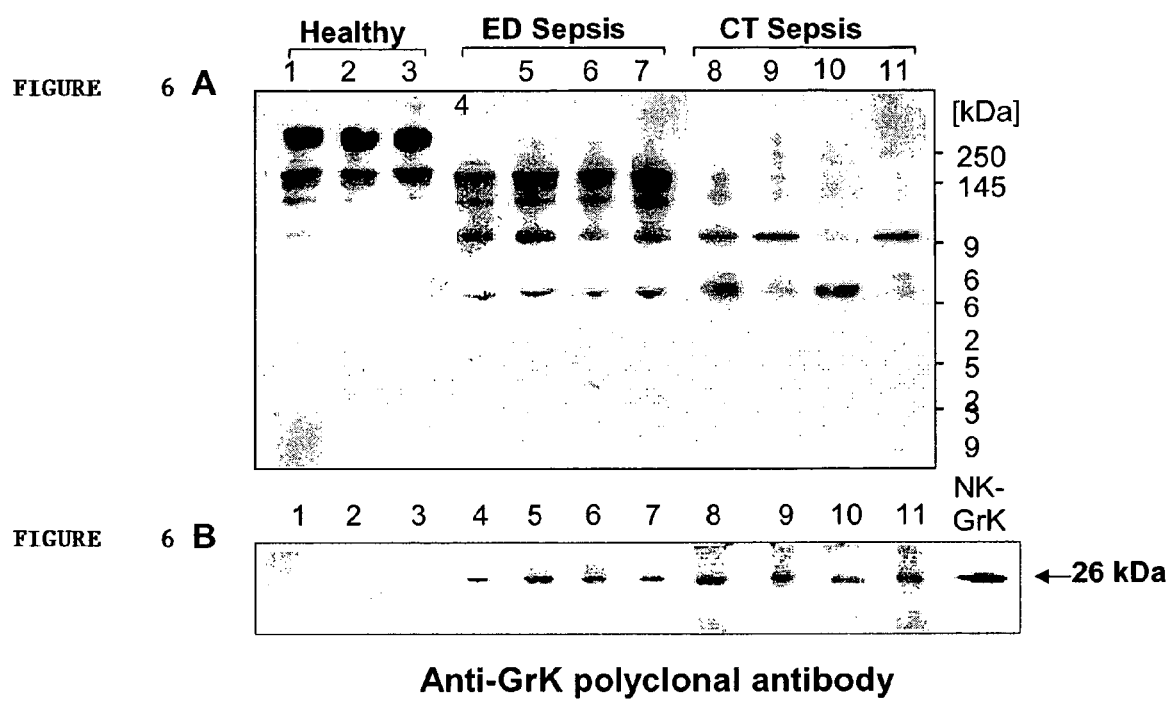
FIGS. 6A and 6B are photographs of electrophoretic gels showing the results of a Western Blot assay. Semi-quantitative Western blot analysis of components detected by anti-GRK polyclonal antibody in human plasma. Plasma samples from healthy controls: HC (lanes 1-3) and septic patient groups: Group ED (lane 4-7) and Group CT (lane 8-11) were analyzed by SDS-PAGE: 4-12% gradient gel (FIG. 6A) or 12.5% single gel (FIG. 6B) under non-reducing conditions, followed by immunodetection with anti-GRK polyclonal antibody. NK-GRK: GRK purified from human NK cells cytotoxic granules was used as a control. Results are representative of at least three experiments.
Figure 9:
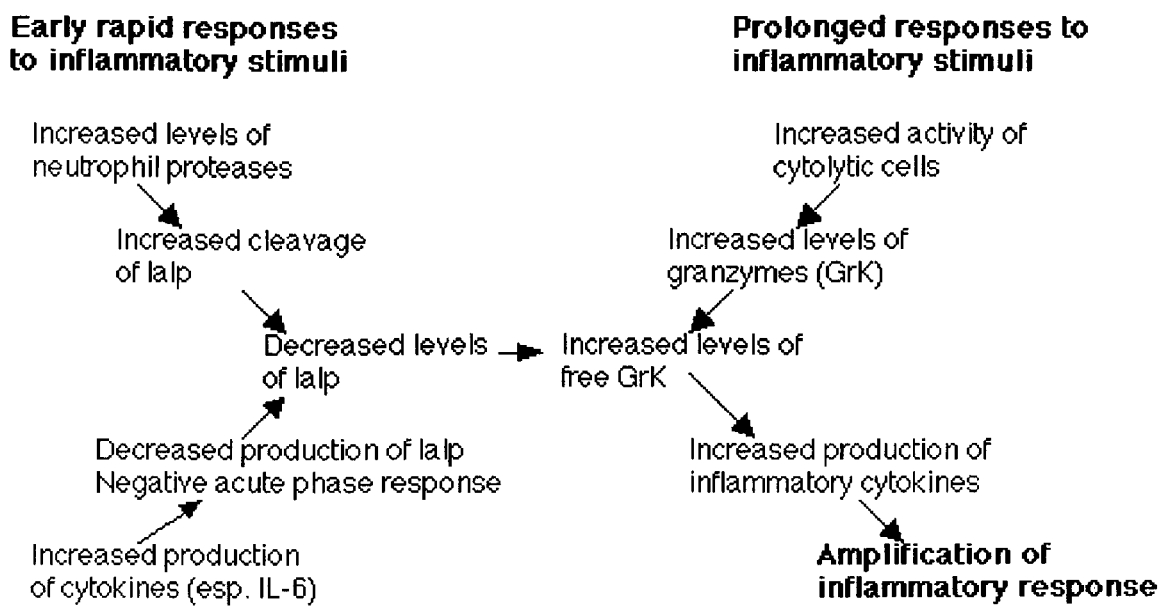
FIG. 9 is a diagram showing the temporal development of responses to inflammatory stimuli.

The monoclonal antibody based assay of Bade et al. is limited in its applicability because it only detects free uncomplexed GRK (FIGS. 6, 9). Because the sequence similarity of the peptide sequence in human and mouse, the antibodies described herein, e.g., the polyclonal antibody, is able to measure human as well as mouse GRK levels. The monoclonal antibody based assay of Bade is unable to do so.

The loss of the GRK inhibitor, inter-alpha-inhibitor protein (IAIP), combined with increased production of GRK via the activation of NK cells results in the appearance of uninhibited GRK which is able to amplify the septic response by the cleavage of specific substrates, and incubation of human peripheral blood lymphocytes with recombinant human GRK results in the production of high levels of IL-6 and IL-8, soluble factors associated with the development of severe sepsis.

GRK Levels in Plasma of Septic Patients: an Early Marker in Sepsis

The assay was tested and found to be highly sensitive and reproducible. For example, GRK concentration in plasma/serum was detected in the range of 15-1000 U/mL. GRK levels were evaluated in healthy normal controls and in patients with sepsis. Plasma was collected from patients enrolled in a septic clinical trial (CT) and septic patients admitted in the Emergency Department (ED). The latter group represents patients with the early stage of sepsis when the diagnosis was established at the time of admission, and the former group represents patients that presented initially as the ED group but had undergone treatment for sepsis. IaIp level in all septic patients were found to be significantly lower than in healthy controls, and GMZK levels were found to be significantly higher in ED patients (mean±SD=1378±189 U/mL, n=15) and significantly lower in CT patients (157±19 U/mL, n=10) compared to healthy controls (747±75 U/mL, n=15). The differences between the septic groups (p<0.0001) and ED to healthy controls (p<0.0015) or CT to healthy controls (p<0.0001) were significant. Western blot analysis confirmed the detection of GRK and revealed a reactive band in human plasma corresponding to approximately 28 kDa in the tested groups.

The results indicate that GRK levels in bodily fluids, e.g., plasma, represent an early marker/diagnostic tool to identify patients that are developing sepsis and are in need of therapeutic intervention.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting sepsis or a risk of developing sepsis in a subject, comprising
contacting a subject-derived sample with an isolated antibody or with a GRK binding fragment of said antibody that binds to both a complex of granzyme K protein (GRK)/GRK inhibitors and uncomplexed GRK, wherein the binding specificity of said antibody or said GRK binding fragment thereof consists of one or more GRK epitope(s) contained in residues 182-197 of SEQ ID NO:1 or residues 189-205 of SEQ ID NO:1,
determining binding of said antibody or said binding fragment to GRK in said sample to determine a level of total or uncomplexed GRK in said sample,
and detecting sepsis or a risk of developing sepsis in the subject by detecting an increase in the level of total or uncomplexed GRK in said subject-derived sample compared to that of a normal control level of GRK.

2. The method of claim 1, wherein said subject is a human.

3. The method of claim 1, wherein said subject is a human infant.

4. The method of claim 1, wherein said sample is blood.

5. The method of claim 1, wherein said sample is plasma.

6. The method of claim 1, wherein said sample is serum.

7. The method of claim 1, wherein said antibody binds to a GRK epitope within the amino acid sequence of NSQSYYN-GDPFITKDM (residues 182-197 of SEQ ID NO:1).

8. The method of claim 1, wherein the antibody is a monoclonal antibody.

9. The method of claim 1, wherein the antibody is a polyclonal antibody.

10. The method of claim 1, wherein the antibody is a mixture of monospecific antibodies.

11. The method of claim 1, wherein said determining step is carried out by immunoassay.

12. The method of claim 1, further comprising determining a level of an inter-alpha inhibitor protein (IaIp) level in said sample, wherein an inverse correlation between an increase in said GRK level and a decrease in IaIp level compared to a normal control indicates a diagnosis of early sepsis.

13. A purified antibody specific for granzyme K protein (GRK), wherein said antibody binds to a GRK epitope within residues 182-197 of SEQ ID NO:1, and wherein said antibody detects free GRK and bound GRK, said bound GRK being a component of a GRK-inhibitor complex.

14. The antibody of claim 13, wherein said antibody binds to both human and mouse GRK.

15. The antibody of claim 13, wherein said antibody is an IgG isotype antibody.

16. A purified antibody specific for granzyme K protein (GRK), wherein said antibody binds to a GRK epitope within residues 189-205 of SEQ ID NO:1, and wherein said antibody detects free GRK and bound GRK, said bound GRK being a component of a GRK-inhibitor complex.

17. The antibody of claim 16, wherein said antibody binds to both human and mouse GRK.

18. The antibody of claim 16, wherein said antibody is an IgG isotype antibody.

19. A method of making a sepsis-detection reagent comprising immunizing an animal with a purified peptide consisting of a GRK epitope contained in residues 182-205 of SEQ ID NO:1 to generate an antibody, isolating said antibody, and, determining binding of said antibody to a GRK epitope within said residues 182-205 of SEQ ID NO:1, wherein detection of said binding indicates that said isolated antibody comprises a sepsis-detection reagent.

* * * * *